US005361436A

United States Patent [19]

Hahn

[11] Patent Number: 5,361,436

[45] Date of Patent: Nov. 8, 1994

[54] PATIENT SUPPORT APPARATUS FOR MEDICAL EXAMINATIONS

[75] Inventor: Alfred Hahn, Erlangen, Germany

[73] Assignee: Siemens Aktiengesellschaft, Munich, Germany

[21] Appl. No.: 107,057

[22] Filed: Aug. 17, 1993

[30] Foreign Application Priority Data

Sep. 2, 1992 [DE] Germany .............................. 4229318

[51] Int. Cl.$^5$ ......................... A61G 7/00; A61G 13/00

[52] U.S. Cl. ........................................ 5/601; 5/610; 378/209

[58] Field of Search ..................... 5/601, 610; 378/209

[56] References Cited

U.S. PATENT DOCUMENTS

| | | | |
|---|---|---|---|
| 2,038,527 | 4/1936 | Wantz | 5/601 X |
| 2,534,623 | 8/1946 | Pitts et al. . | |
| 2,707,137 | 4/1955 | Hallstein | 5/610 |
| 2,775,496 | 12/1956 | Berggren | 5/601 |
| 3,240,935 | 3/1966 | Dougall | 5/601 X |
| 3,804,109 | 4/1974 | Weber et al. . | |
| 4,045,078 | 8/1977 | Shine . | |
| 4,333,637 | 6/1982 | Shelton . | |
| 4,450,575 | 5/1984 | Mueller | 378/26 |
| 4,653,683 | 3/1987 | Rossi | 378/196 |
| 4,795,142 | 1/1989 | Schaefer . | |

FOREIGN PATENT DOCUMENTS 2260986 9/1975 France .

*Primary Examiner*—Michael F. Trettel

*Attorney, Agent, or Firm*—Hill, Steadman & Simpson

[57] ABSTRACT

A support apparatus for supporting and positioning a patient during a medical examination includes a patient support plate and a combination of elements for lifting and pivoting the support plate which operate to pivot the support plate around a stationary, virtual (i.e., non-load bearing) axis disposed at an end region of the support plate.

4 Claims, 4 Drawing Sheets

PATIENT SUPPORT APPARATUS FOR MEDICAL EXAMINATIONS

BACKGROUND OF THE INVENTION

1. Field of the Invention

The present invention is directed to a patient support apparatus of the type used to support and position a patient during a medical examination.

2. Description Of the Prior Art

Patient support systems are known in the art which include a patient support plate and elements which are attached to, and act on, the support plate to lift and pivot the support plate. Such a table is disclosed for x-ray examinations in U.S. Pat. No. 2,534,623. This support table is pivotable around a load-bearing axis disposed in a mid-region of the support plate. In order to maintain the space required by this x-ray table as small as possible, a lifting mechanism is provided which lifts the axis of the table while the table is being pivoted around that axis. Proceeding from a horizontal position, the table can thus be pivoted into a vertical position with a low space requirement.

During anglographic examinations, it is frequently necessary to transirradiate a vessel from different directions for producing an image. If the patient support table is to be pivoted for this purpose, it is necessary that the table be pivotable around a stationary region. The aforementioned known x-ray table does not have a region which remains stationary during pivoting.

SUMMARY OF THE INVENTION

It an object of the present invention to provide a patient support apparatus for use in conducting medical examinations of the type having a patient support plate for an examination subject which is pivotable around a stationary region.

The above object is achieved in accordance with the principles of the present invention in a patient support apparatus having a support plate with lifting and pivoting elements attached to the support plate forming, in combination, means for pivoting the support plate around a stationary, virtual axis, which is disposed at an end region of the support plate.

As used herein, the term "virtual axis" means an imaginary axis which can be visualized in space as a point around which the support table pivots, however, the axis is not formed by a mechanical element and is thus not a Icad-bearing axis.

An advantage of the patient support apparatus of the invention is that the support plate can be pivoted around a stationary region, so that the apparatus can be used in angiographic examinations.

DESCRIPTION OF THE PREFERRED EMBODIMENTS

Figure 1:
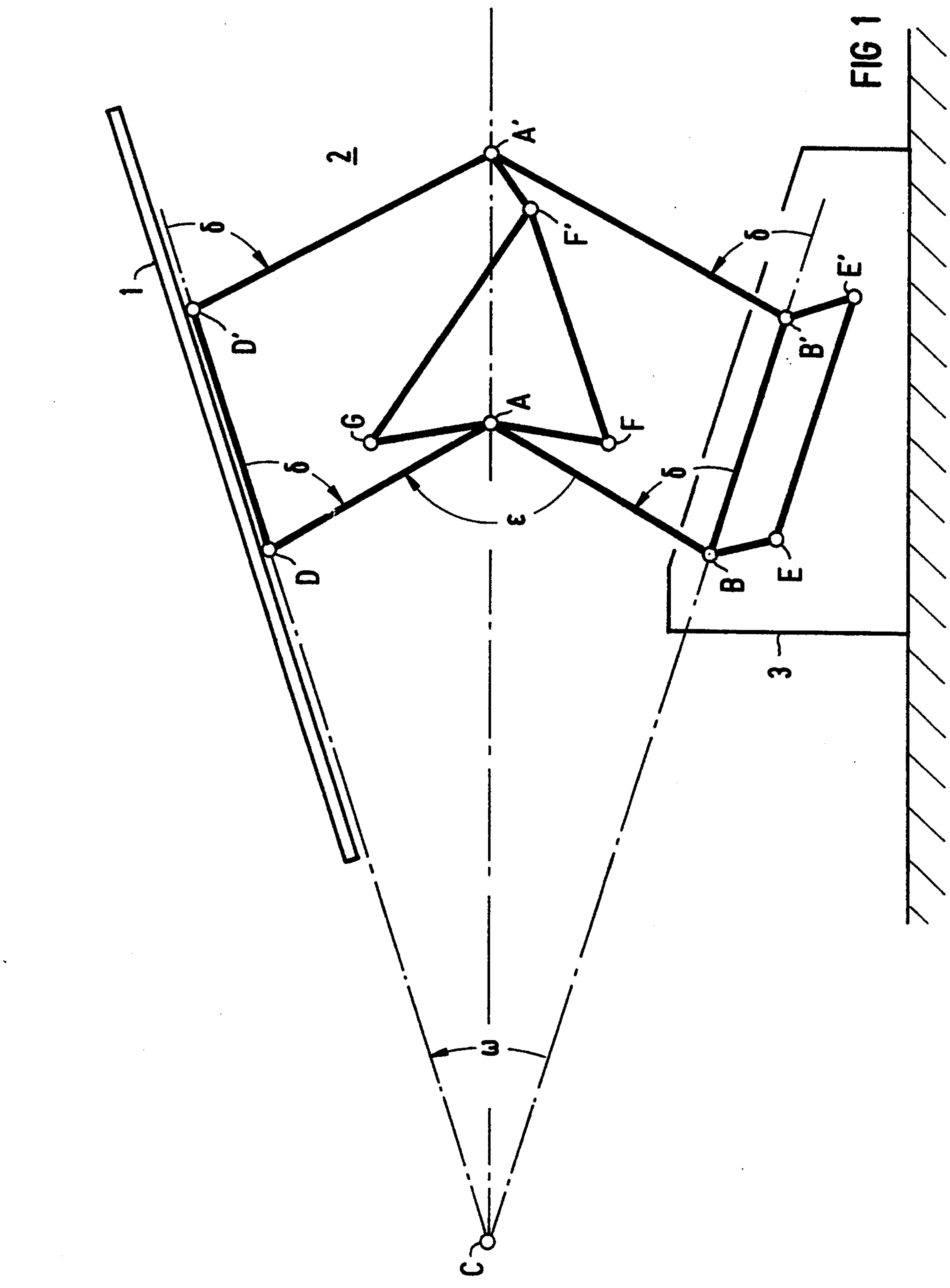
FIG. 1 is a schematic illustration of a first exemplary embodiment of a patient support apparatus constructed in accordance with the principles of the present invention.

FIG. 1 shows a schematic representation of a patient support apparatus constructed in accordance with the principles of the present invention, for use in explaining the structure and operation of the physical embodiments of the invention. The apparatus as schematically shown in FIG. 1 includes support plate 1 which is connected by an articulated lever arrangement 2, forming a lifting and pivoting means, to a base 3 disposed on the floor of an examination room. The support plate 1 is pivotable around a stationary, virtual axis C, located at an end region of the support plate 1=In order to achieve such pivoting around the stationary, virtual axis C, the articulated lever arrangement 2 must satisfy the following principles. The articulated lever arrangement 2 is composed of two pairs of similar triangles ABC-/A'B'C and ACD/A'CD',which are connected mirror-symmetrically. The segments DA and DD' have an angle δ therebetween, as do the segments BA and BB'. When the angle δ changes, the distances AC and A'C, but the distances BC and CD remain constant. The remaining, lower (AB/A'B') and upper (AD/A'D') pairs of triangle sides are maintained parallel to each other by means of two coupling arms E/E' and F/F', and are articulated so as to operate in the opposite direction with respect to a third coupling arm F'G such that the two angles δ remain approximately the same.

The patient support apparatus thus includes lifting and pivoting means in the form of a lever arrangement, wherein the levers of the lever arrangement are fashioned in the configuration of first and second trapezoids, with the sets of parallel sides in each trapezoid (AD/A'C' and AB/A'B') being of different lengths, and the trapezoids having a common third side (AA'), and a fourth side (DD') of the first trapezoid is in communication with the support plate 1 and a fourth side BB' of the second trapezoid is in communication with the base 3, as a pedestal.

Figure 2:
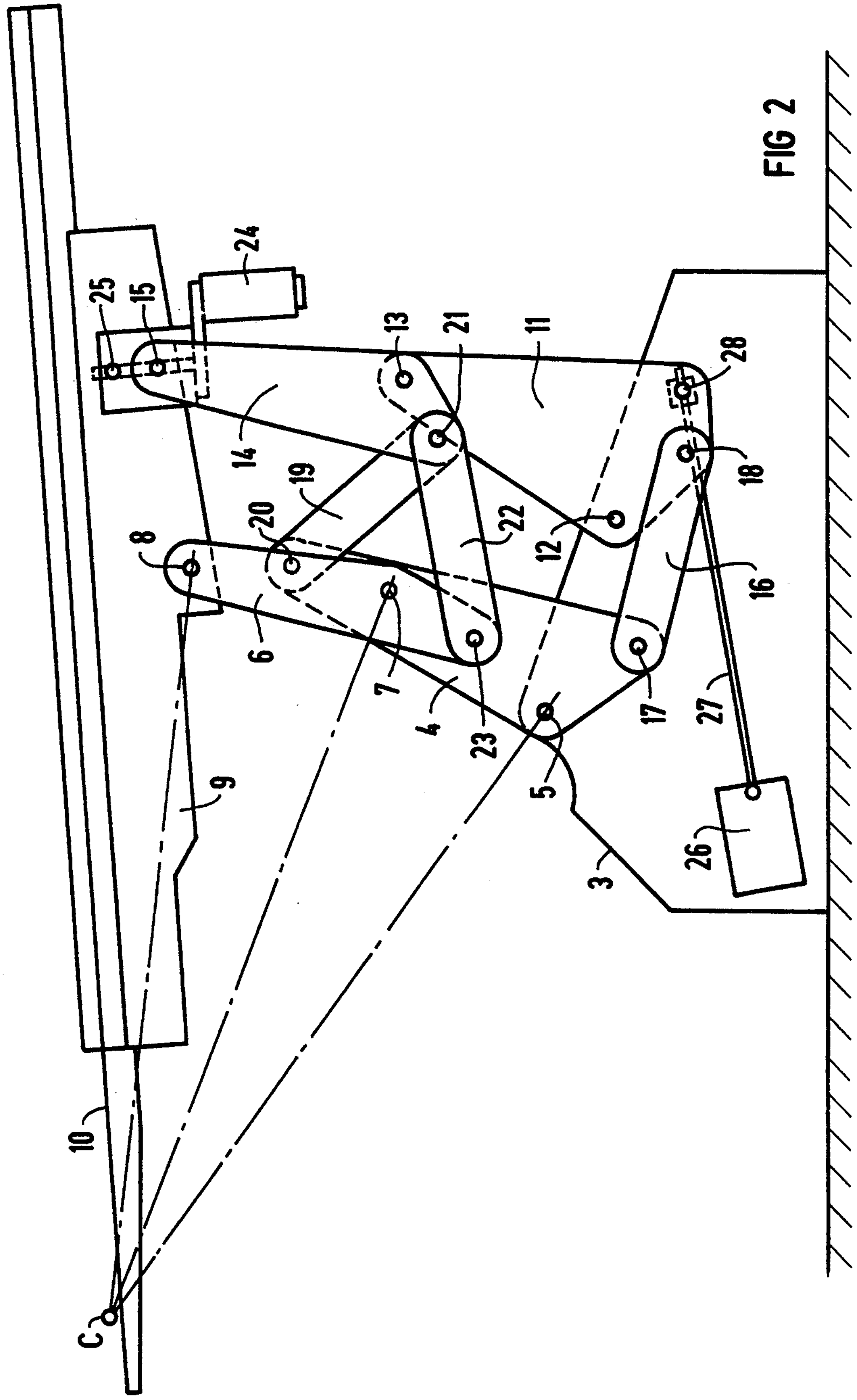
FIG. 2 is an embodiment of a patient support apparatus physically embodying the schematic principles shown in FIG. 1.

The patient support apparatus of FIG. 1 with the articulated lever arrangement 2 is shown in further detail in FIG. 2. Elements which have already been provided with a reference numeral in FIG. 1 are provided with the same reference numeral in FIG. 2. In FIG. 2, a first lever arm 4 is pivotable around a first axis 5 at the base 3. A second lever arm 6 has a common, second axis 7 with the first lever arm 4, and is connected to a holder 9 for a support plate 10 via a third axis 8.

The first axis 5, the second axis 7 and the stationary, virtual axis C, around which the support plate 10 is pivotable, thus form the first triangle of the similar triangle pair BAC/DAC, with the second triangle being formed by the second axis 7, the third axis 8 and the stationary virtual axis C. The triangles of the pair BAC/DAC are joined mirrorsymmetrically, as shown in FIG. 1. Analogous to the segment B'A' in FIG. 1, a third lever arm 11 is provided in the embodiment of FIG. 2, which is mounted so as to be pivotable around a fourth axis 12 at the base 3. The end of the third lever arm 11, analogous to the path A'B' in FIG. 1, is connected via a fifth axis 13 to a fourth lever arm 14, which has an opposite end connected to a sixth axis 15 at the holder 9. The first and third lever arms 4 and 11 are connected to each other via a first coupling element 16 and a seventh axis 17 and an eighth axis 18. The upper end of the first lever arm 4 (facing toward the bearing plate 10) and a lower end of the fourth lever arm 14 are connected via a second coupling element 19 and a ninth axis 20 and a tenth axis 21. The lower end of the first lever arm 14 and the lower end of the second lever arm 6 are connected via a third coupling element 22 and the tenth axis 21 and an eleventh axis 23. The first and seventh axes 5 and 17 together with the fourth and eighth axes 12 and 18, form the sides of a first parallelogram, these sides being connected via the first coupling element 16. Similarly, the third and eleventh axes 8 and 23, together with the sixth and tenth axes 15 and 21, form the sides of a second parallelogram, which are connected via the third coupling element 22.

A first electromechanical adjustment device 24, for example, a motor and gear box, operates on a twelfth axis 25 of the holder 9 in the embodiment of the patient support apparatus shown in FIG. 2, for effecting a relative displacement of the sixth and twelfth axes 15 and 25 with respect to each other. The sixth axis 15 has no connection to the holder 9. The distance of the surface of the bearing plate 10 from the stationary, virtual axis C can thus be varied by operation of the electromechanical adjustment device 24.

Pivoting of the support plate 10 around the stationary, virtual axis C is effected by a second electromechanical adjustment device 26, which may also be a motor and gear box, which is mounted at the base 3 and which operates on a thirteenth axis 28 at the third lever arm 11. The second electromechanical adjustment device 26 can operate on the thirteenth axis 28, for example, by means of a spindle drive 27.

In an embodiment of the patient support apparatus of FIG. 2 which is reduced in scale, the first and seventh axes 5 and 17 have a spacing of 160 millimeters, the first and second axis 5 and 7 have a spacing of 295 millimeters, the paths formed by the axes 5 and 17, and 5 and 7, assume an angle of 109° relative to other, the spacing between the second and ninth axis 7 and 20 is 148 millimeters, and the angle between the segments formed by the first and second axes 5 and 7 and by the second and ninth axes 7 and 20 is 158°. The distance between the eleventh and second axes 23 and 7 is 148 millimeters and the distance between the second and third axes 7 and 8 is 295 millimeters, with the segments thus formed assuming an angle of 156° relative to one another. The distance between the seventh and eighth axes 17 and 18 as well as between the eleventh and tenth axes 23 and 21 is 300 millimeters, and the distance between the ninth and tenth axes 20 and 21 is 290 millimeters. The segment formed by the fourth and eighth axes 12 and 18 has a length of 160 millimeters and assumes an angle of 112.41° relative to the segment formed by the fourth and fifth axes 12 and 13, which is 373 millimeters in length. The distance between the fourth and thirteenth axes 12 and 28 is 220 millimeters and the segment therebetween assumes an angle of 87° relative to the segment between the fourth and fifth axes 12 and 13. The distance between the tenth and fifth axes 21 and 13 is 100 millimeters, and the segment therebetween assumes an angle of 122.59° relative to segment formed by the fifth and sixth axis 13 and 15, which has a length of 373 millimeters.

Within the context of the invention, of course, the articulated lever arrangement may be formed by differently configured lever arms and axes as well as coupling elements, as along as the condition is satisfied that the support plate 10 is pivotable with a lifting and pivoting means around a stationary, virtual axis C disposed at the end region of the support plate 10. Although the lifting and pivoting means moves in the sense of pivoting at the articulation points, the overall arrangement does not move from the base 3 during lifting and pivoting of the support plate 10.

Figure 3:
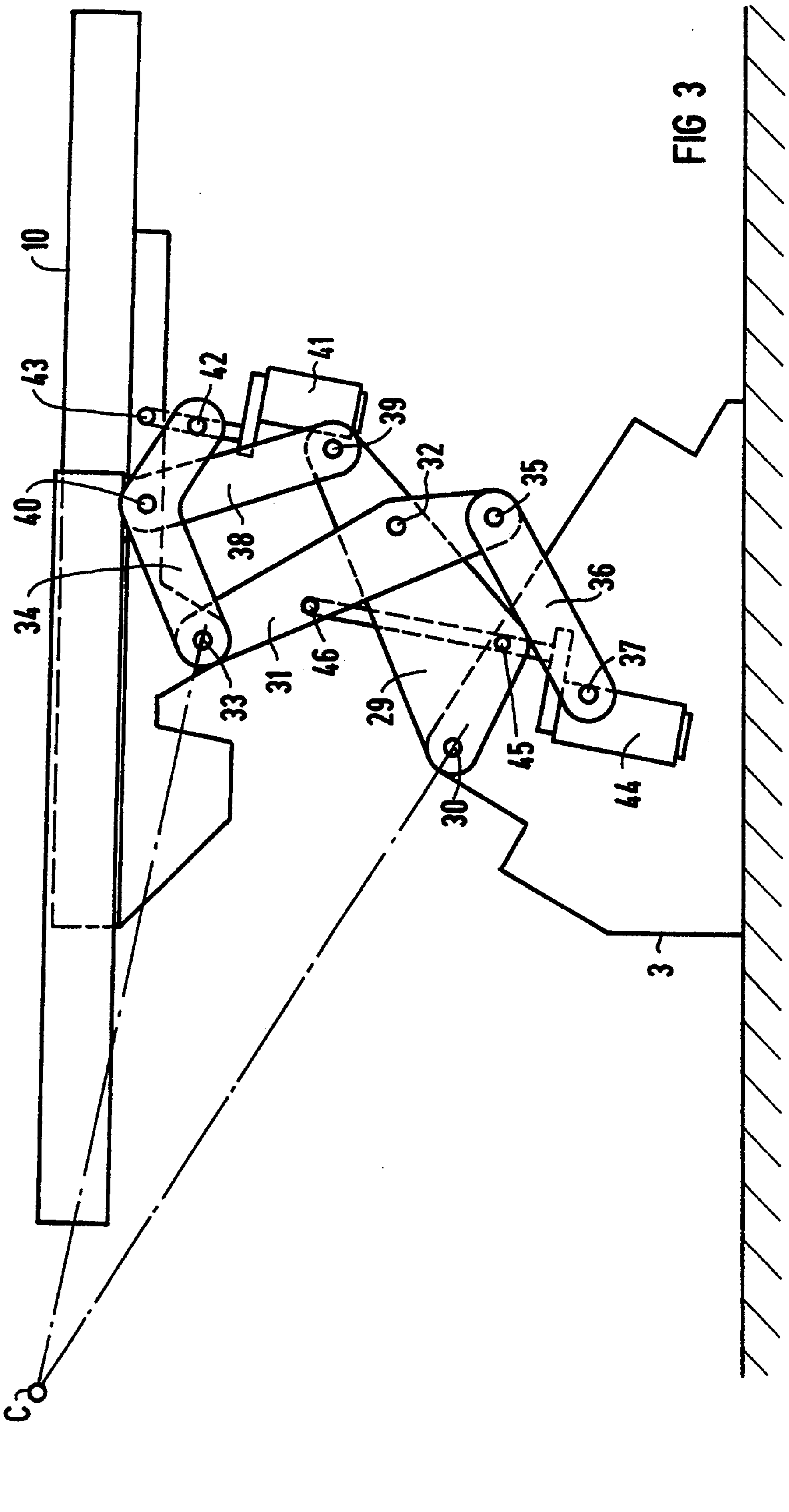
FIG. 3 is a further embodiment of patient support apparatus physically embodying the schematic principles shown in FIG. 1.

Another exemplary embodiment of a patient support apparatus constructed in accordance with the principles of the present invention is shown in FIG. 3. The embodiment of FIG. 3 is structurally more simple in comparison to that of FIG. 2. In the embodiment of FIG. 3, a first lever arm 29 is pivotable around a first axis 30 at the base 3. A second lever arm 31 has a common, second axis 32 with the first lever arm 29, and is connected at a first end to a third lever arm 34 via a third axis 33, and at an opposite end to a fourth lever arm 36 via a fourth axis 35. The fourth lever arm 36 is pivotable around a fifth axis 37 at the base 3. The first and third lever arms 29 and 34 are connected via a fifth lever arm 38 and sixth and seventh axes 39 and 40. The support plate 10 is supported at the third axis 33. A first electromechanical adjustment device 41, such as a motor and a spindle, operates on an eighth axis 42 of the third lever arm 34, and on a ninth axis 43 of the support plate 10, so that the distance of the surface of the support plate 10 from the stationary, virtual axis C can be set thereby.

A second electromechanical adjustment device 44 engages a tenth axis 45 of the first lever arm 29, and an eleventh axis 46 of the second lever arm 31.

The effective radii of the coupling points 35 and 37, and 39 and 40, and the angles relative to the mid-line are selected so that the condition $\epsilon=2\delta-\omega$(see FIG. 1) is satisfied with optimum precision. This condition is satisfied when the spacing between the first and second axis 30 and 32, or between the second and third axes 32 and 33, is selected such that the maximum angle assumed by the respective segments defined by these axes in the useful region is no greater than 90°. Moreover, the effective radii must be sufficiently large so that the bearing forces remain in the permissible range given the maximum possible load on the support plate 10 and maximum lift.

Adjustment of the lever articulation beyond the useful range will cause a lifting of the support plate 10 out of the axis C, so that a slight geometrical enlargement, as well as a larger useful field, for example, at the x-ray image intensifier, are obtained for peripheral angiography. The height of the support plate 10 can be reduced by combining the first and second electromechanical adjustment devices 41 and 44.

Figure 4:
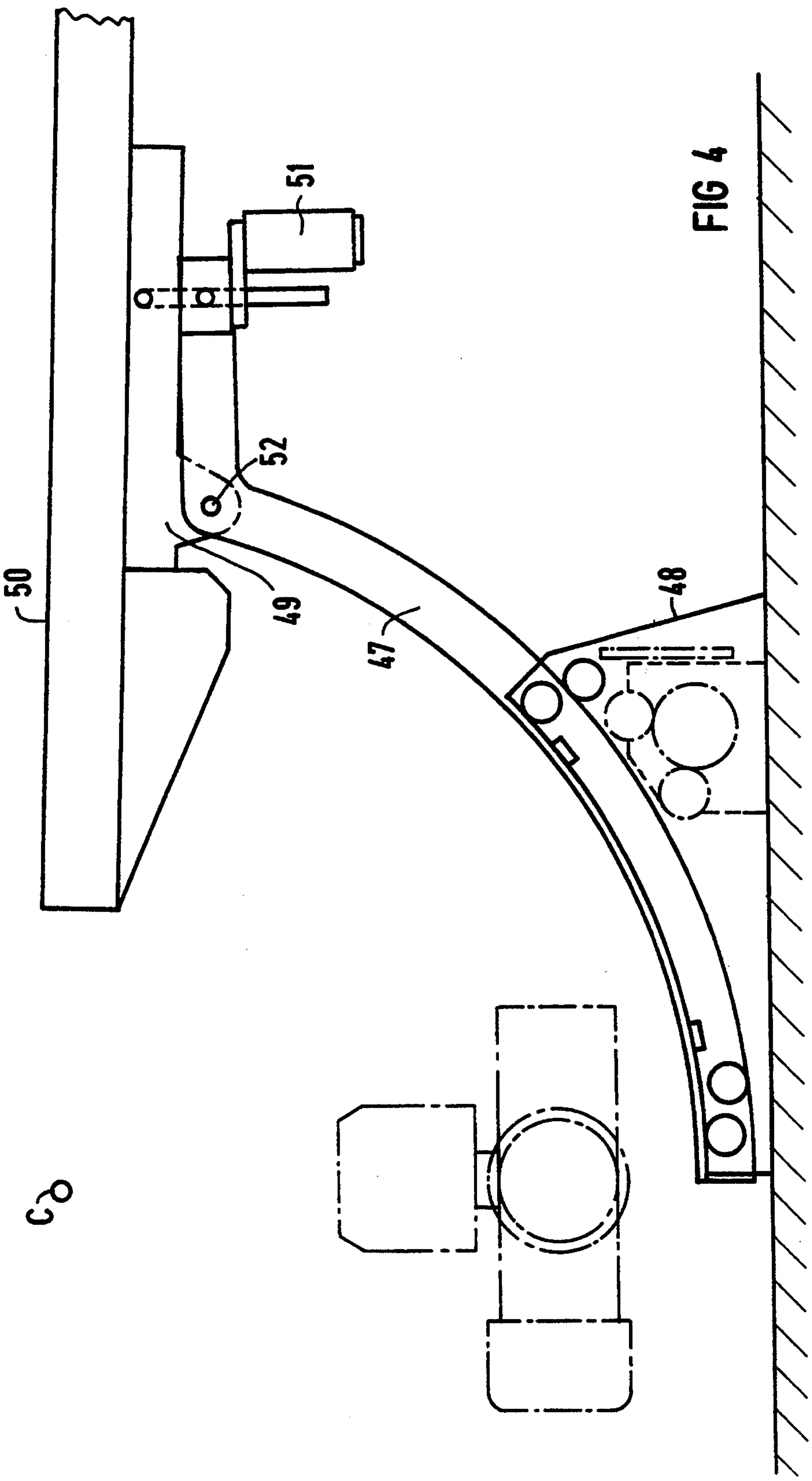
FIG. 4 is a third embodiment of a patient support apparatus constructed in accordance with the principles of the present invention employing an arc.

A further exemplary embodiment of a patient support apparatus of the invention is shown in FIG. 4, having an arc 47 which is adjustable along its circumference at a base 48. A support plate 50 is mounted at one end of the arc 47 by a holder 49. The arc 47 is a substantially circular segment of a circle having a center at the stationary, virtual axis C, which is at the end region of the support plate 50. When the arc 47 is pivoted along its circumference, the support plate 50 is also adjusted around the stationary, virtual axis C. A first electromechanical adjustment device 5 17 for pivoting the support plate 50 around a pivot bearing 52 at the end of the arc 47 is engaged at the holder 49.

Without departing from the inventive concept the pivoting of the support plate around the stationary, virtual axis C can ensue by separate lifting and pivoting means operating on the support plate, each being driven by electromechanical means so that the desired pivoting of the support plate around the stationary, virtual axis C is accomplished.

In an x-ray diagnostics installation having an x-ray radiator and a radiation receiver mounted opposite each other at respective ends of a C-arm, and being pivotable around an isocenter, the stationary, virtual axis C is aligned parallel to a transverse axis of the patient support apparatus and preferably intersects the isocenter. This permits the examination subject to be transirradiated from different directions by adjusting the patient support apparatus.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for supporting a patient during an examination, comprising:

a patient support plate having opposite ends; and lifting and pivoting means attached to said patient support plate for lifting said support plate and pivoting said support plate around a stationary., virtual axis disposed at an end of said patient support plate.

2. An apparatus as claimed claim I wherein said lifting and pivoting means comprises an articulated lever arrangement system.

3. An apparatus as claimed claim 2 wherein said articulated lever arrangement system includes a plurality of levers including a first group of levers forming a first trapezoid and a second group of levers forming a second trapezoid, said first trapezoid having a set of parallel sides of different lengths and said second trapezoid having a set of parallel sides of different lengths, said first trapezoid having first and second parallel sides of different lengths and said second trapezoid having first and second parallel sides of different lengths, said first and second trapezoids each having a third side which is shared in common by said first and second trapezoids, and said first trapezoid having a fourth side adjacent to said patient support plate and said second trapezoid having a fourth side adjacent to a support pedestal for said system.

4. An apparatus as claimed claim I wherein said lifting and adjustment means comprises a circular arc mounted for sliding movement along its circumference, said circular arc having a center coinciding with said stationary, virtual axis.

* * * * *